United States Patent [19]

Andrews et al.

[11] Patent Number: 5,718,861
[45] Date of Patent: Feb. 17, 1998

[54] METHOD OF FORMING INTRA-AORTIC BALLOON CATHETERS

[75] Inventors: Robert R. Andrews, Norfolk; William Edelman, Sharon; Joseph A. Levendusky, Groton; Peter T. Majeski, Cambridge, all of Mass.; Robert L. O'Brien, Rindge, N.H.

[73] Assignee: C. R. Bard, Incorporated, Murray Hill, N.J.

[21] Appl. No.: 484,894

[22] Filed: Jun. 7, 1995

Related U.S. Application Data

[60] Division of Ser. No. 210,611, Mar. 18, 1994, abandoned, which is a continuation-in-part of Ser. No. 170,513, Dec. 20, 1993, abandoned.

[51] Int. Cl.$^6$ .................... B29C 41/14; B29C 71/02
[52] U.S. Cl. .................... 264/235; 264/301; 264/334
[58] Field of Search .................... 264/235, 301, 264/334, 346

[56] References Cited

U.S. PATENT DOCUMENTS

| | | | |
|---|---|---|---|
| 4,531,512 | 7/1985 | Wolvek et al. | 600/18 |
| 4,543,090 | 9/1985 | McCoy | 604/95 |
| 4,646,719 | 3/1987 | Neuman et al. | 600/18 |
| 4,665,906 | 5/1987 | Jervis | 606/78 |
| 4,758,222 | 7/1988 | McCoy | 604/95 |
| 4,934,340 | 6/1990 | Ebling et al. | 600/151 |
| 4,994,018 | 2/1991 | Saper | 600/18 |
| 4,994,047 | 2/1991 | Walker et al. | 604/264 |
| 4,998,917 | 3/1991 | Gaiser et al. | 604/96 |
| 5,042,985 | 8/1991 | Elliott et al. | 606/192 |
| 5,067,957 | 11/1991 | Jervis | 606/108 |
| 5,087,394 | 2/1992 | Keith | 264/22 |
| 5,090,957 | 2/1992 | Moutafis et al. | 604/96 |
| 5,120,308 | 6/1992 | Hess | 604/95 |
| 5,129,890 | 7/1992 | Bates et al. | 604/281 |
| 5,156,612 | 10/1992 | Pinchuk et al. | 606/194 |
| 5,190,546 | 3/1993 | Jervis | 606/78 |
| 5,195,969 | 3/1993 | Wang et al. | 604/96 |
| 5,304,340 | 4/1994 | Downey | 264/521 |

OTHER PUBLICATIONS

"Super Elasticity—Superelastic Tinel® Alloys", Raychem (undated).

"A New Technique for Sheathless Percutaneous Intra–Aortic Balloon Catheter Insertion", Nash et al., Catherizaton and Cardiovascular Diagnosis 23:57–60 (1991).

*Primary Examiner*—Leo B. Tentoni
*Attorney, Agent, or Firm*—Wolf, Greenfield & Sacks, P.C.

[57] ABSTRACT

A method of forming intra-aortic balloons includes forming a balloon blank having a sleeve section at its proximal end. To reduce the diameter of the sleeve section of the balloon, the sleeve section is stretched longitudinally by gripping a first portion of the balloon blank at the distal end of the sleeve section, gripping a second portion of the balloon blank at the opposite end of the sleeve section and moving at least one of the gripped portions away from the other so as to reduce the diameter of the sleeve section. A heating element is positioned within the sleeve section to relieve the stress in the sleeve after stretching, by heating the sleeve section. The sleeve section is then cooled in order to preserve the sleeve section in its reduced diameter state thereby forming an intra-aortic balloon having a balloon blank with a reduced diameter sleeve section.

9 Claims, 4 Drawing Sheets

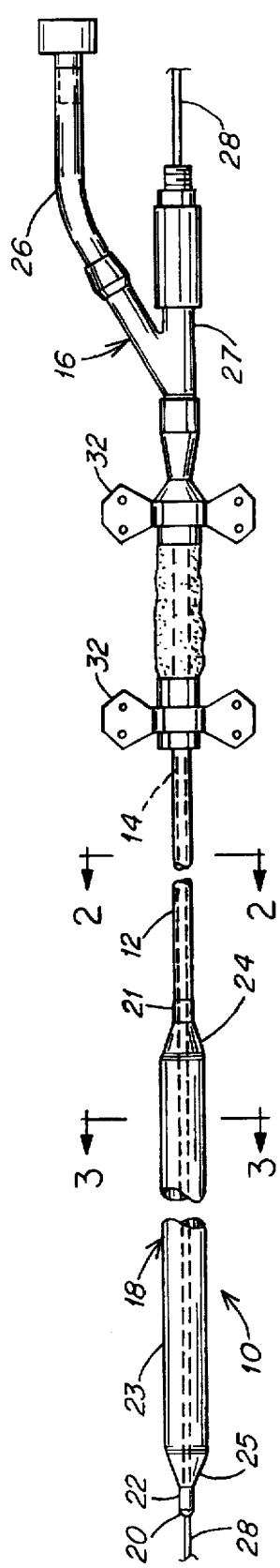
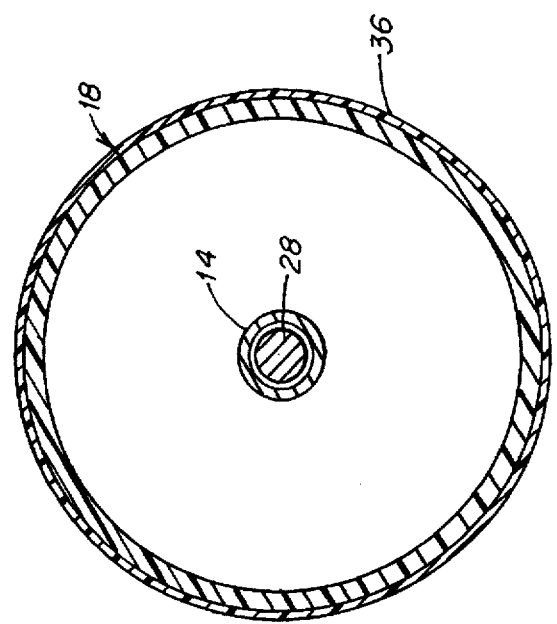
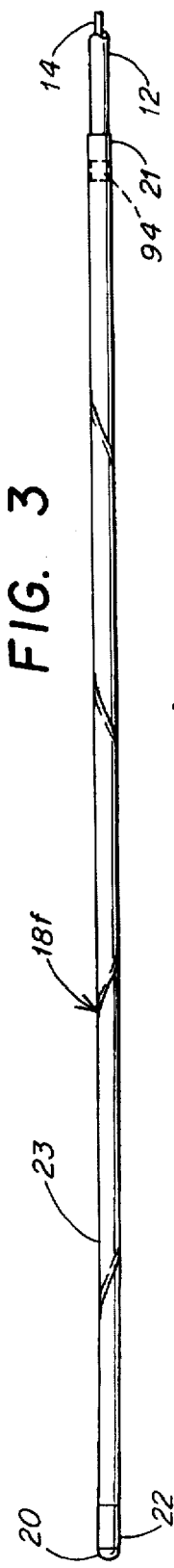
FIG. 1
FIG. 2
FIG. 3
FIG. 4

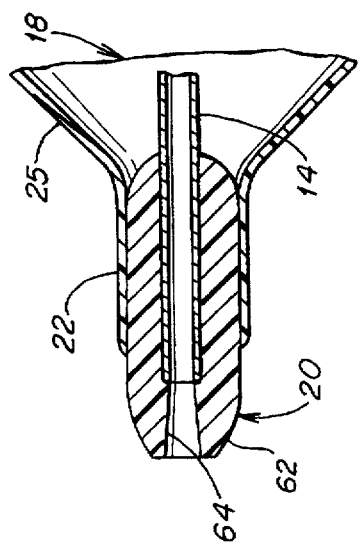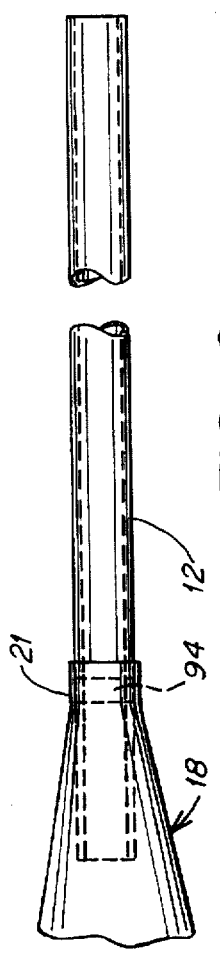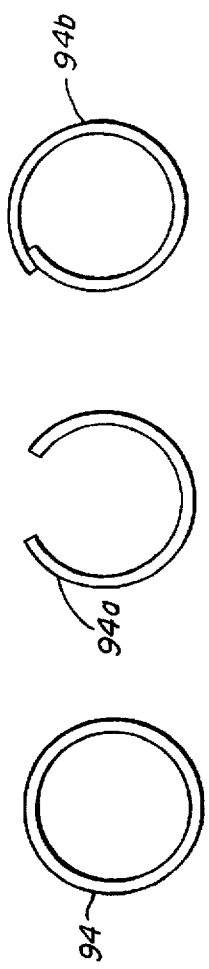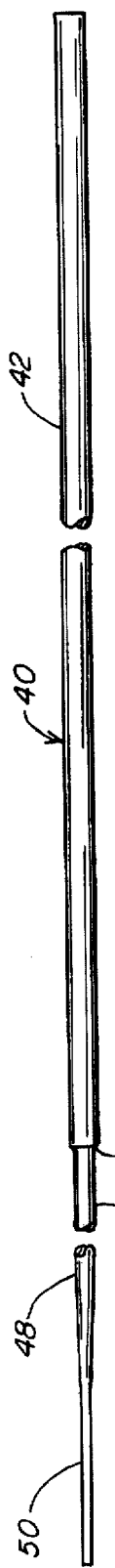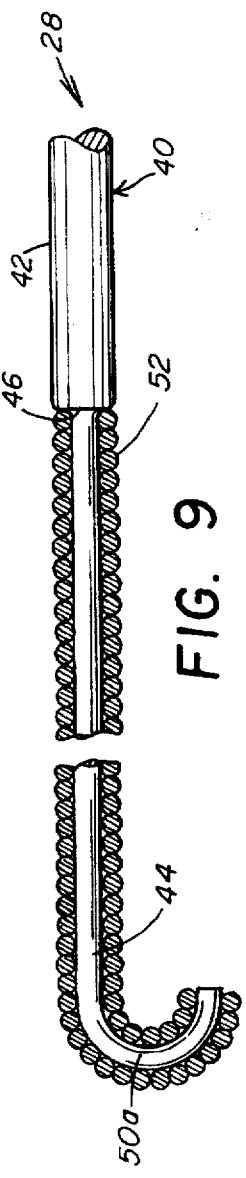

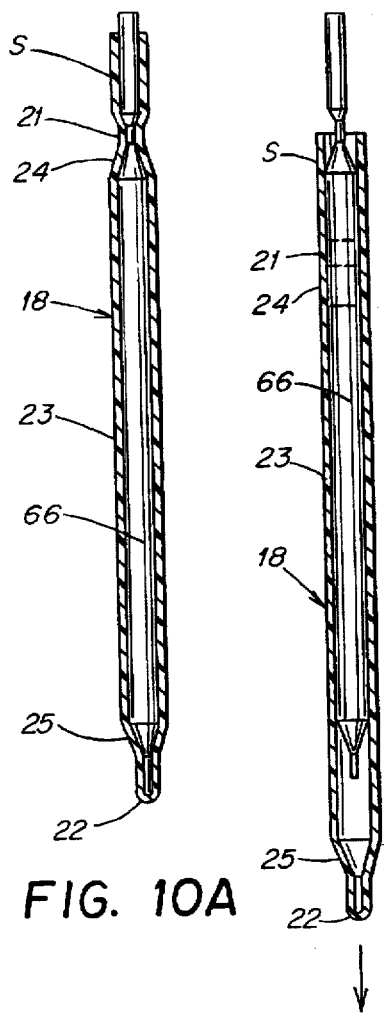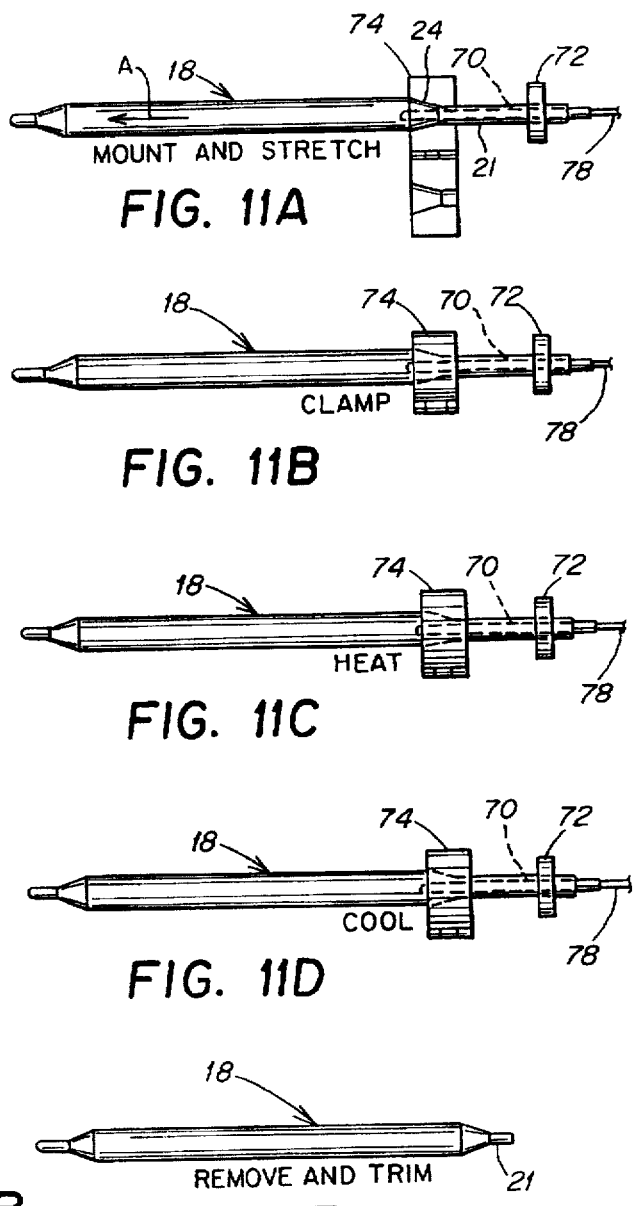

METHOD OF FORMING INTRA-AORTIC BALLOON CATHETERS

This application is a divisional of Ser. No. 08/210,611 filed Mar. 18, 1994 which is a Continuation-In-Part of Ser. No. 08/170,513 filed Dec. 20, 1993, both of which are now abandoned.

FIELD OF THE INVENTION

This invention relates to intra-aortic balloon pumps and particularly to improved intra-aortic balloon pump catheters.

BACKGROUND OF THE INVENTION

Intra-aortic balloon pumps (IABP) are used to provide counter pulsation within the aorta of ailing hearts over substantial periods of time, e.g. to provide ventricular assistance during cardiogenic shock, low cardiac output in postoperative care, weaning from cardiopulmonary bypass, treatment for refractory unstable angina, and other circumstances of sub-normal cardiac function. Such pumps of the type involved in this invention include a flexible intra-aortic balloon (IAB) which is readily inflatable under low pressure to substantial size and displacement. The balloon is mounted on a catheter device used for insertion of the balloon into a remote artery, typically a femoral artery, and through the intervening vascular system of the patient to the aortic pumping site while the balloon is deflated and furled. This requires insertion of the furled large capacity balloon through a small insertion passage, e.g., a small puncture opening or through an introducer cannula into the selected artery, and then sliding-threading of the catheter and furled balloon through tortuous lumen passageways of the patient's vascular system over a guidewire to the pumping site, e.g. from insertion into an artery in the groin area to the patient's descending aorta. At the pumping site, the balloon is unfurled and then successively and rapidly inflated and deflated in synchronism with the patient's cardiac pulsation rates over extended periods of time in a known counterpulsation technique to enhance cardiac output. Thus, use of an IABP requires forceful sliding insertion of a relatively large balloon through a small insertion opening and tortuous arterial lumens, which may be randomly narrowed by arteriosclerotic deposits of plaque, and subsequent unfurling and reliable pulsation operation at heartbeat rates over substantial periods of time, e.g. for several days.

It will be appreciated that the circumstances and requirements of insertion and use of intra-aortic balloon pumps provide numerous conflicting parameters. Significant aspects of these conflicting parameters are related to the fact that the inflated but unstretched diameter of the balloon is much larger than the diameter of the insertion site, which may be percutaneous, and larger than at least portions of the lumen of the vascular system through which it is to be threaded. This requires that the balloons be furled for insertion through passageways which are of very small inside diameter (ID) relative to the size of the balloon when opened. The related catheter equipment typically must include dual concentric lumens, including an inner lumen passageway to serve functions such as engaging over a guidewire, sensing values in the aorta, e.g. arterial pressure, and/or administration of medicaments. A surrounding annular passageway between the inner and outer lumens must be of a size adequate to shuttle an operating gas such as helium at rates to obtain the rapid repetitious expansion and collapse of the balloon necessary for the pumping function in counterpulsation to the patient's heart.

The aforenoted parameters for intra-aortic balloon catheters have resulted in these catheters being of significant complexity of construction and attendant substantial size, i.e. substantial effective diameter of the catheter structure during insertion as well as during the periods of pumping operation within the patient's vasculature. A significant potential complication during use is associated with limb ischemia due to size mismatch between the overall size (diameter) of the counter pulsation catheter and the effective lumen size of the patient's vasculature through which the catheter must pass and in which it must remain during the period of pumping assistance. Heretofore, the full featured IAB catheter systems available on the market have been of nominal 9 French (Fr) size or larger. The Fr size designation of an IABC refers to the approximate size of the outer lumen. Thus, for example, while 9 Fr literally is about 0.118" diameter, catheters designated as 9 Fr may have outer lumens which slightly exceed that dimension, e.g., up to about 122". Further, such catheters may include balloons which originally were furled to about 0.126" outer diameter and in which the furling has relaxed to about 0.144" outer diameter in their packaging sheaths. In any event, reduction in size of intra-aortic balloon catheters and introducer systems would improve systemic flow to limbs at risk.

However, as indicated above the insertion of an IAB catheter intrinsically involves pushing the device along a tortuous path through the patient's vasculature. This requires applying and transmitting compressive forces through the very slender "column" structure of the catheter, which requires a significant degree of stiffness in the catheter. The catheter also must flex or bend to follow the desired path through the patient's vasculature without undue lateral reactive force which could cause trauma to the vessels. Thus IAB catheters should have a high degree of stiffness over a wide range of bending angles, while providing flexibility to follow tortuous paths along which the IAB catheter is being pushed. These characteristics are measures of the "pushability" and "trackability" of the catheter, e.g., to follow a guide wire when pushed therealong over a tortuous path without overcoming the guiding stiffness of that wire and/or otherwise impinging on the vasculature walls with potentially injurious forces.

IAB catheters also must resist kinking, i.e., sharp bending collapse of either or both of the lumen tubes with attendant loss of smooth curvature and closing or drastic reduction of the respective internal passageway. Resistance to kinking is necessary to maintain pushability of the catheter assembly and to avoid binding on the guide wire. Avoiding kinking also minimizes risks of cracking of the lumens during insertion and attendant risks of later leakage during operation, as well as minimizing risks of kink-blockage of the gas shuttle capacity between the lumens or blockage of medication or sensing operations through the inner lumen during pumping operation.

It is an object of this invention to provide improved intra-aortic balloon pump catheters.

It is a more specific object of this invention to provide such catheters wherein adequate gas shuttling capacity can be obtained with conventional pump controllers through catheters of significantly reduced size.

Similarly, it is an object of this invention to provide such improved catheters wherein substantially higher gas flow rates and attendant higher shuttle speeds may be obtained in catheters of sizes used heretofore, thereby permitting tracking of heart rhythms not trackable with conventional previous catheters.

It is a further object to provide improved IAB catheters which attain some or all of the aforegoing objects and which maintain high degrees of flexibility, torquability, pushability and trackability for safe and easy insertion, with minimal risk of trauma to the patient.

SUMMARY OF THE INVENTION

It has been found that IAB catheters using very small metal lumen tubes having high degrees of elasticity and particularly shape restorative elasticity will satisfy the aforementioned parameters. This will allow flexibility with stiffness over a wide range of bending angles of IAB catheters, down to quite severe bends and other temporary deformations which may occur in the course of insertion or operation. More particularly, it has been found that by fabricating IAB catheters with at least the inner lumen being a superelastic thin walled metal tube such as of nitinol, the inner lumen can have a very thin wall with an inside diameter (ID) sufficient for a guidewire and a small outside diameter (OD) which allows reduction of the outer lumen and related components by at least one size Fr while providing gas shuttle capacity between the lumens for conventional IAB pump operation. This design also attains excellent flexibility and stiffness of the catheters for ease of insertion and assurance of functionality while reducing the outside diameter to significantly reduce the risks of vascular and ischemia complications.

As used herein, the terms "superelastic alloy" or "superelastic alloys" and "superelasticity" refer to those materials, specifically those metal alloys, which return to their original shape upon unloading after a substantial deformation. In most if not all instances superelasticity is related to shape memory. It is understood that a shape memory alloy is one which displays a thermoelastic martensitic transformation and is able to absorb several percent shear strain by preferential orientation of martensite variants, and then can reverse that shear strain upon being heated, as the martensite transforms back to the parent (austenits) phase. Similarly, it is understood that a superelastic alloy is the same as a shape memory alloy except that it absorbs strain above the transformation temperature by the creation of stress-induced martensite variants of preferential orientation, and then reverts to the parent phase at the same temperature as reduced stress reverses the strain. Superelastic alloys can be strained up to ten times more than ordinary spring materials without substantial permanent deformation, i.e., less than 0.5%. They provide nearly constant stress forces over a wide range of elastic deformation, as represented by typically "flag shaped" stress-strain curves, without significant change of temperature.

Nitinol (nickel-titanium alloys) is perhaps the best known of these materials. Its tranformational superelasticity is about ten times higher than elasticity in ordinary materials. Further, various nitinol alloys are known which are superelastic within the temperature ranges of the living human body. One further description of the superelasticity characteristic and of nitenol alloys which provide this characteristic at human body temperatures appears in a publication of Raychem Corporation entitled *"Superelasticity— Superelastic Tinel® Alloys"*, which is incorporated herein by this reference and a copy of which is being filed with this application.

Further, it has been found that improved forms of the outer lumen may be provided of co-extruded plastics to complement and enhance the size reduction and capacity goals noted above. In the preferred embodiment this includes a relatively thin major inner nylon portion for strength and a polyurethane outer portion for biocompatability, flexibility and compatibility for bonding to the balloon.

Improved techniques for production of appropriate balloons and for joining the respective components also are provided, particularly for joining of each balloon to the distal end of the outer lumen and to the distal end of the inner lumen while avoiding or minimizing buildup of diametral dimensions. Moreover, it has been found that intra-aortic balloons may be made with thinner walls than heretofore to further complement the aforenoted results without compromising the integrity of the system. A radiopaque metal marker ring also has been provided which is compatible with the size reduction goal while providing improved imaging capabilities.

BRIEF DESCRIPTION OF THE DRAWINGS

FIG. 1 is a simplified top view of an intra-aortic balloon catheter employing this invention.

FIG. 2 is an enlarged cross-sectional view taken along line 2—2 of FIG. 1.

FIG. 3 is an enlarged cross-sectional view taken along line 3—3 of FIG. 1, on a lesser scale than FIG. 2.

FIG. 4 is an enlarged side elevation view of the balloon portion of the catheter with the balloon furled, such as for insertion.

FIG. 5 is an enlarged sectional view of a portion of the catheter assembly at the distal end of the balloon, taken along an axial diametral plane.

FIG. 6 is an enlarged side view of the outer lumen and adjacent proximal end portion of the balloon of the catheter of FIG. 1.

FIG. 7 is an end view of a radiopaque tracer ring included in the catheter of FIG. 1.

FIGS. 7A and 7B illustrate alternative configurations of the tracer ring.

FIG. 8 is a side view of a stylet used in forming the guidewire of the catheter of FIG. 1.

FIG. 9 is an enlarged side view of the outer end of the guidewire used in the catheter of FIG. 1.

FIGS. 10A and 10B schematically illustrate the stripping of intra-aortic balloons from mandrels on which they have been formed by dip casting.

FIGS. 11A–E are schematic illustrations of steps for reforming the proximal end sleeve portions of such balloons.

Figure 12:
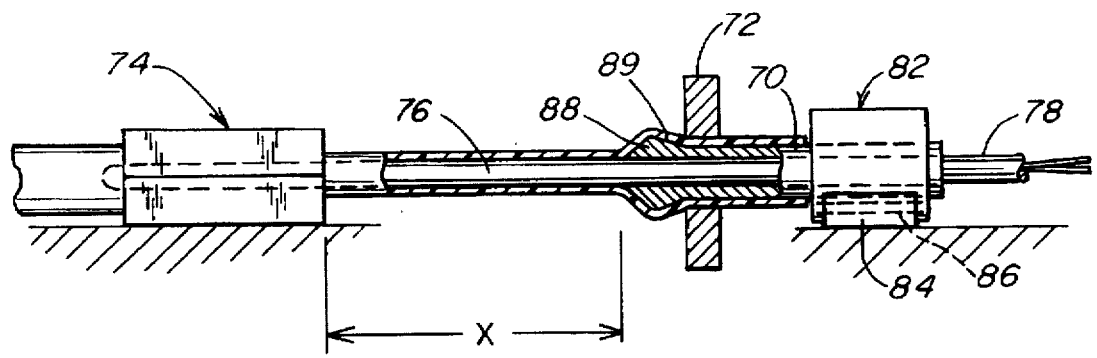
FIG. 12 is a schematic side view of one preferred apparatus used in the process illustrated by FIGS. 11A–E.
Figure 13:
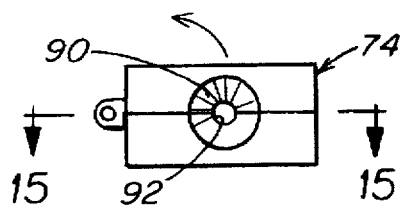
FIG. 13 is a left-end view of the balloon clamp of FIG. 12.
Figure 14:
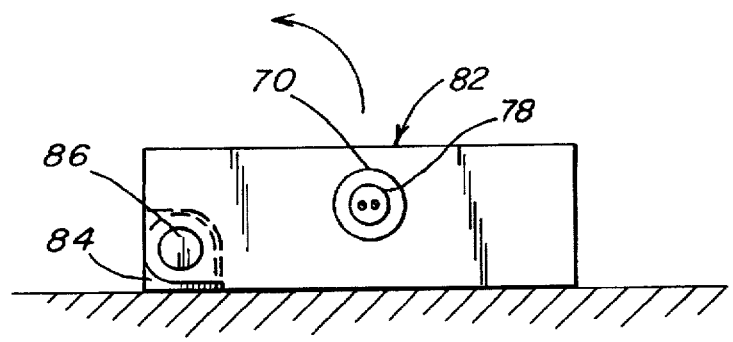
FIG. 14 is a right-end view of the apparatus of FIG. 12.
Figure 15:
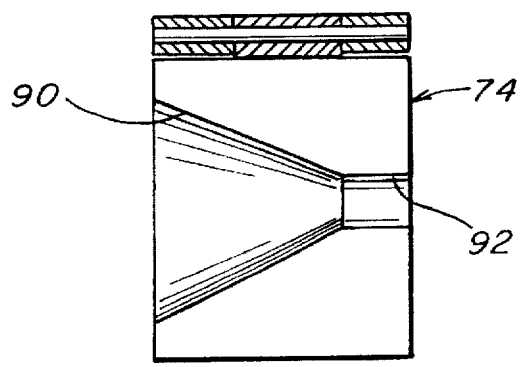
FIG. 15 illustrates the shape of the cavity defined by the balloon clamp, as seen generally along line 15—15 of FIG. 13.

While the invention will be further described in connection with certain preferred embodiments, it is not intended to limit the invention to those embodiments. On the contrary, it is intended to cover all alternatives, modifications and equivalents as may be included within the spirit and scope of the invention.

DETAILED DESCRIPTION OF PREFERRED EMBODIMENTS

As illustrated in FIG. 1, one embodiment of an intra-aortic balloon pump catheter device 10 includes a flexible outer lumen tube 12 and a co-axial flexible inner lumen tube 14 which are attached to a wye connector 16. The inner lumen tube 14 extends through the outer lumen 16 and through a single chamber intra-aortic balloon 18 to the distal tip end of the catheter. The proximal end of the balloon 18 is attached to the distal end of the outer lumen tube 12. The distal end of the balloon 18 is attached to a compatible tip element 20 on the distal end of the inner lumen tube 14. Each of these balloon-lumen attachments is a gas-tight solvent bond connection between an end sleeve section 21,22 of the balloon and the outer surfaces of the outer lumen 12 and the tip 20, respectively. As seen in the drawings, these end attachment sleeves are of substantially lesser diameter than the main displacement body section 23 of the balloon and are joined thereto by short tapered sections 24,25.

The wye connector 16 provides access through the lateral branch 26 to an appropriate gas supply pump and control device (not shown) for inflating and deflating the balloon 20 by successively injecting and withdrawing a gas such as helium through the annular space between the lumens 12 and 14. As indicated above, this is sometimes referred to as "shuttling" the inflation gas to and from the balloon. The controller responds to signals corresponding to the pulsing of the heart and effects inflation and deflation of the balloon in timed counterpulsation to the pumping action of the heart in a known manner. The axial section 27 of the wye provides axial access to the inner lumen for reception of a guide wire 28 as well as for sensing of arterial pressure and/or the injection of medicaments through the inner lumen. Tie downs 32 are included for affixation to the skin of the patient by suturing and/or taping for securing the catheter in its inserted operative pumping position.

The balloon 18 is a large flexible thin-film balloon of conventional appropriate size, i.e., on the order of about 0.5" to about 1.0" in diameter when in an inflated but unstretched condition and about 8" to 12" in length. Typical sizes are of 30 cc, 40 cc and 50 cc displacement. The balloon may be formed of any suitable material, with polyurethane presently being preferred. A hydrophilic coating 36 preferably covers the balloon and forms a lubricous outer surface which is very slippery when wetted by an aqueous fluid, such as blood, while permitting processing and furling of the balloon and handling of the balloon and related pump mechanism in a normal manner when dry. Presently preferred coatings and appropriate modes of applying such coatings are disclosed in co-pending application Ser. No. 08/170,513, filed Dec. 20, 1993, the disclosure of which is incorporated herein by this reference.

The balloon 18 is furled, as illustrated schematically at 18f in FIG. 4. This minimizes its effective outer diameter during insertion into a patient's arterial system. The furling may be accomplished in a conventional manner. This includes applying a solution of silicone and freon on the outer surface such as by spraying to deposit silicone thereon, then evacuating the air from the balloon thereby causing the balloon to collapse into flat generally radially extending "wings", then rolling those wings tightly about the inner lumen 14 in mutually interleaved relation with one another. This winds the collapsed balloon "wings" into tightly packed spirals as viewed in cross-section, to minimize the effective outer diameter of the balloon during handling and during the insertion process. The silicone avoids surface-to-surface sticking of the furled layers. A thin tubular packaging sheath typically is placed over each furled balloon to maintain its furled compaction to a minimum effective outside diameter during shipping and handling, up to the place and time of insertion into the patient. Further, the furled balloons typically are heated, e.g., to a temperature on the order of about 135° F. for about 12-16 hours, to assist in setting and thereby sustaining the furling during insertion following removal from the packaging sheath by the user. Balloons with the noted hydrophilic coatings also become very slippery promptly upon being wetted, with attendant benefits of ease of insertion and placement as well as reduction of trauma.

The wye connector 16 and related components and equipment may be of any suitable structure and size.

The inner lumen 14 is a very thin-walled tube formed of a tough and superelastic metal, namely nitinol. For example, it has been found that an inner lumen tube 14 of such materials having a wall thickness of only about 0.0035" will function satisfactorily in providing a small IAB catheter, e.g., 8 Fr size. The inner lumen tube 14 minimizes the outside diameter of the inner lumen while maintaining the necessary functional inside diameter as well as providing desirable characteristics of flexibility and strength throughout the length of the catheter.

An exemplary such inner lumen tube 14 has about 0.0276" ID and 0.0345" OD. By comparison, the inner lumen currently used in the 9 Fr IAB catheters being marketed by the Cardiac Assist Division of St. Jude Medical, Inc., under the trademark RediGuard™, consist of a polyurethane tube of about 0.008" wall thickness surrounded by a coiled stainless steel wire of 0.003" diameter generally as in the arrangement disclosed in U.S. Pat. No. 4,646,717, resulting in an effective overall thickness of the inner lumen wall of 0.011" and an attendant OD of 0.054" to provide an inner lumen ID of 0.032".

The outer lumen tube 12 is formed by coextrusion of a thin outer polyurethane layer around a thicker nylon inner layer 12b. The nylon layer provides high compressive strength relative to the thickness, and it is believed that the polyurethane layer provides flexibility as well biocompatability and compatibility for ready bonding of the polyurethane balloon. One advantageous combination has been found to be a 0.002" outer layer of polyurethane coextruded with a 0.006" inner layer of nylon, with the total wall thickness being about 0.008". Thus the outer lumen 12 also is a relatively thin-walled tube, as compared to current commercial polyurethane outer lumens which are on the order of 0.010" thick.

By utilizing inner and outer lumens 12 and 14 as described, the annular space therebetween is of adequate cross-section to accommodate the gas shuttle capacity required for normal IABP operations using a conventional controller while minimizing the outside diameter of the catheter, e.g., reduction of the catheter by one full size Fr, and meeting the other desirable parameters for IAB catheters. Concomitantly, IAB catheters using this construction and of the same nominal size as prior constructions would be capable of higher gas shuttle rates than those prior devices and thus capable of tracking higher heart pulsation rates.

The outer lumen also could be formed of a thin walled metal tube having superelasticity, for example also being formed of nitinol. This alternative would permit further reduction of the outer diameter of the outer lumen while maintaining equivalent or even better operational capabilities, but would add significantly to the costs at the present price of nitinol tubing. Referring particularly to FIGS. 8 and 9, the guidewire 28 is of a stylet-type with a "floppy J" tip, similar to some guidewires utilized heretofore in other applications, e.g. in cholangiography (catheterization of bile ducts). The stylet 40 is a slim rod or wire which includes a main body portion 42 normally of uniform circular cross-section and a distal end portion 44 of modified configuration for forming the "J" tip. For example, the distal end portion is significantly reduced in diameter along the second portion 44, with an annular shoulder 46 between portions 42 and 44. Sequentially outward of the section 44 is a third portion 48 which is tapered to a lesser diameter, and an end portion 50 which is flattened in cross-section. As represented in FIG. 9, the proximal end of a fine wire 52 is brazed or welded to the stylet shaft adjacent the shoulder 46. The wire extends in closely wound coil fashion about the distal portion 44, with the distal end being brazed or welded to the distal tip of the stylet body 42. The distal end portion 50a is bent approximately 180°, preferably being bent normal to the flattening planes, to form the bight of the "J" tip, generally as illustrated.

By way of further example, one guidewire 28 for use in one specific embodiment of this invention as described herein included a stylet 40 formed of 302/304 stainless steel, about 150 cm in length and with the shoulder 46 being about 30 cm from the distal end. The main body portion 42 was about 0.025" in diameter. Second portion 44 was about 0.013" in diameter and extended for about 23 cm from the shoulder 46. Portion 48 was tapered from the 0.013" diameter to about 0.0055" diameter over a length of about 6 cm, and the distal end 3 cm portion was flattened to about 0.0035" thickness. The wire 52 was about 0.005" diameter, also being of 302/304 stainless steel. The distal 3 cm was bent to form the bight and remote leg of the "J" tip. The entire assembly was coated with Teflon, providing a guidewire with a diameter not exceeding 0.025" for use through the inner lumen described above.

As noted above, the balloon 18 may be of the same material, configuration and size as balloons currently in use in intra-aortic balloon pumps. An example of a preferred embodiment includes a thin-walled polyether based polyurethane balloon of about 0.003"–0.004" wall thickness formed by dip molding on an appropriately shaped mandrel, with a hydrophilic coating as referred to above. This is a reduction of about 0.001 thickness from balloons currently in commercial use. Such balloons have satisfactory flexibility and strength, with high elasticity, e.g., about 525% stretchability without rupture. One specific commercially available polyurethane which has proven satisfactory in such balloons, including those used in practicing this invention, is sold by B. F. Goodrich under the designation "Estane 58810".

Referring particularly to FIG. 5 an end tip 20 is affixed over the outer end of the inner lumen tube 14, as by being molded thereonto. For this purpose, the outer surface of the end portion of the tube may be sandblasted as a preparatory step. The tip 20 preferably is of a plastic which is compatible with the material of the balloon, e.g., polyurethane. The outer end surface 62 of the tip is rounded in a bullet-nose shape to facilitate passage through the patient's vasculature. The outer end portion has a central axial passage 64 which provides a smooth continuation of the central axial passage of the lumen tube 14 and preferably tapers or flares toward the distal end of the tip, as illustrated in FIG. 5. This passage section 64 may be formed by a core pin being positioned in the outer end of the lumen tube 12 prior to the molding of the tip 20.

Referring now to FIGS. 1, 5 and 6, the cylindrical proximal sleeve portion 21 of the balloon 18 is bonded to the outer surface of the distal portion of the outer lumen 12 and the cylindrical distal sleeve portion 22 of the balloon is bonded to the outer surface of the tip 20. These bonds must be airtight and effected in a manner to minimize the diametral dimension build-up of the catheter assembly. Such bonding is facilitated by forming the tip 20 and at least the outer surface of the outer lumen 12 and the balloon 18 of the same types of materials, namely polyurethane in the illustrated preferred embodiment. In this embodiment, the sleeve portions 21 and 22 are bonded to the respective elements by a solvent and pressure-bonding technique. It is believed that pressure-bonding with radiofrequency heating to a temperature approximating the melting temperature of the materials will further enhance this bond and provide even greater control and minimizing of the final outer dimensions in these bonding areas. The intervening portion of the balloon 18, including the larger body section 23, is tightly furled about the inner lumen tube 14 between the distal end of the inner lumen 12 and the tip 20. With the thin-walled balloon referred to above, this multi-layered furled portion will have an outer diameter which only slightly exceeds the outer diameter of the sleeve attachment sections. This is an added factor in maintaining the minimal profile of the entire catheter assembly during insertion.

Referring to FIGS. 10A and 10B, the balloons 18 are made by dip casting on a mandrel 66 having a shape corresponding to the inflated unstretched shape of the balloon 18, including the end sleeve sections 21,22, generally as seen in profile in FIG. 1 and 10A. The dipping speed and time are adjusted to produce thin-walled balloons as referred to above. Each of the balloon blanks as thus formed also includes an end section S which extends from the sleeve 21 over the mandrel hanger generally as illustrated, and which subsequently is trimmed from the blank. The formed balloons are stripped from the respective mandrels by axial movement toward the distal end, whereby the proximal sleeve 21 and adjacent tapered portion 24, as well as section S, are stretched in diameter as they slide over the much larger central portion of the mandrel on which the main balloon body portion 23 was formed, as illustrated schematically in FIG. 10B. This stretching of the proximal ends results in proximal end sleeves that are not reliably of a sufficiently small inner diameter to provide the desired snug fit of the balloon on the small outer lumen tubes 12 for facile formation of the necessary air-tight joint at this interface. Accordingly, the production of the balloons preferably includes reduction of the size of the proximal end sleeves after removal of the balloons from the casting mandrels.

Referring to FIGS. 11A–11E and 12, the section S and sleeve portion 21 of each balloon blank are mounted over an internal mandrel 70 and secured in place by a collet 72. The balloon is stretched to a predetermined length of the proximal sleeve section 21, as indicated by the arrow A in FIG. 11A. The balloon then is held in the stretched state to maintain the desired sleeve length, as by a hinged clamp 74 which engages the cone section 24 of the balloon, as in FIG. 11B. The stretching causes the intervening sleeve to neck down to the desired reduced diameter, as indicated in FIGS. 11A and 11B. At this point the neck is in a stressed state. At least the sleeve section of the balloon is heated, as by an internal heater cable 76 which is positioned with the mandrel 70 (see FIG. 11C), to an appropriate temperature over an appropriate dwell time thereby relaxing the necked-down balloon material in its reduced size configuration. That is, the stress induced by the stretching is relieved. The balloon then is permitted to cool to a normalizing temperature while in the reduced, non-stressed configuration, as by turning off the power to the heater; see FIG. 11D. This precludes subsequent elastic return of the sleeve portion 21 to its previous oversize diametral dimension. The balloon with the reduced diameter proximal end sleeve 21 then is removed from the clamp and mandrel, and the end section S is trimmed off as in FIG. 11B.

One mechanism for effecting the foregoing is illustrated in somewhat greater detail in FIGS. 12–15. A mandrel 70 is mounted in a support block 82 which is pivotally mounted to a fixed support 84 as by an appropriate pivot pin 86 located adjacent one end of the block 82, with the pivot pin offset from the mandrel 70. The heating cable 78 extends through the mandrel 70 to a pin shaped heating element 76. An intervening portion of the mandrel 70 has a bulbous section 88, with an annular outer surface 89 which tapers to smaller diameters toward the support block 82. The collet 72 is of an annular or "washer" shape, having an internal surface which conforms to the tapered surface of the mandrel. The clamp 74 comprises two hinged mating halves defining therebetween a truncated conical open section 90 communicating with a short small cylindrical section 92, which correspond generally to the configuration of the transitional section 24 and desired sleeve section 21 of the balloons being processed.

In operation, to practice the aforedescribed method, the clamp 74 is opened in preparation for receiving a balloon to be processed. The collet 72 is retracted toward the heater cable base block 82. The block 82 is pivoted to an upper position (about 90° counterclockwise) in FIG. 14, to raise the mandrel/heater further from a support surface on which the components are mounted and thereby providing greater space for the following described manipulations. The distal end portion of a balloon then is slid onto the mandrel unit 70, from the left end in FIG. 12, with the distal end portion of the sleeve section S over the enlarged section 88 and onto the tapered section 89. The collet 72 is then moved towards the enlarged section 88, to provide friction clamping of the balloon end S between the inner surface of the collet and the outer tapered surface of the mandrel. The balloon is then stretched, e.g. manually by the operator, to the point where the tapered end section 24 will match up with the cavity defined by the sections 90 of the clamp halves, thereby suitably reducing the diameter of the neck or sleeve section 21. The heater cable base block 82 is closed, and the balloon is positioned with the tapered end section 24 mating into the cavity defined by the sections 90 of the clamp halves, with the sleeve section stretched over the intervening internal mandrel and heater 76. The clamp 74 then also is closed to retain the sleeve section of the balloon in the resulting stretched state. Internal to the balloon at this point is the heater coil 76, which extends the entire length of the sleeve area and slightly into the balloon body area, as seen in FIG. 12. Subsequently, the heater is activated to thereby relax the necked down balloon material as described above. Following heating and subsequent cooling, the clamp 74 is opened and the collet 72 released, and the balloon is removed. The section S then is cut off. A distal end portion of the stretched sleeve also may be trimmed to attain the desired length of sleeve 21 which now has the desired reduced inner diameter. The internal mandrel/heater may be utilized as the form for setting the size of the reformed sleeve section 21. By way of more specific example, in a typical operation the sleeve portion 21 has been stretched to about 150% of its original length in this process, e.g., stretched from 0.5" to 0.75," to effect the desired reduction of the diameter of the neck in polyurethene balloons as described hereinabove.

It will be appreciated that other gripping and stretching mechanisms may be utilized to effect the sleeve sizing method. For example, one and/or the other of the clamping mechanisms 74 and 72,88 may be movable toward and away from the other whereby the balloon blank may be clamped therein prior to stretching and then may be stretched by lateral movement of one or both of the clamping mechanisms relative to the other.

Referring to FIGS. 6 and 7, radiopaque marker material is applied to the outer lumen 12 in a position to be adjacent the proximal end of the balloon in the final assembly. This permits the user to readily determine the location of the balloon by fluoroscopy or X-ray, as necessary to attain maximum therapeutic benefit. In a preferred embodiment this marker is a thin short ring 94 of highly elastic metal such as nitinol, being the same material as the inner lumen. Use of the same metal for the marker and the lumen avoids any problems of incompatibility of dissimilar metals, such as electrokinetic corrosion of either element, while providing a highly radiopaque and therefore highly visible marker for the positioning of the IAB during use. By using a thin short ring 94 of nitinol, e.g. 0.003" thick and 0.075" long, the marker may be press-fit in place in the outer lumen 12 and the compression of the lumen will hold the ring in place. The balloon is bonded over the outer lumen 12, preferably with the sleeve 21 of the balloon over the marker ring 94, and is furled tightly over the inner lumen tube 14 as noted above. The high degree of elasticity of the ring permits the marker to deform in the process of packaging and insertion while assuring return to its nominal desired shape and size in use. Splitting the ring longitudinally so that it is discontinuous circumferentially, with the ends either spaced or overlapping as illustrated at 94a and 94b in FIGS. 7A and 7B respectively, will enhance its hoop compressibility by a resilient spring action and thus further complement the size reduction as well as flexibility of the catheter unit.

In a specific example of the preferred embodiment of this invention, a nominal 8 Fr IAB catheter 10 was fabricated with an inner lumen tube 14 formed of a nitinol alloy tubing of Raychem Corporation designated Tinel Alloy BB formed of only nickel and titanium and only those trace elements naturally occurring in commercially available grades of those constituents. The tube 14 had a nominal inner diameter of 0.0276" a nominal outer diameter of 0.0345", and a length of 32.775". The outer tube 12 was a coextrusion of 2363-55D Pelletbane polyurethane (Dow Chemical Company, Midland, Mich.) 0.002" thick over Nylon 11 Besno (Elf Atochem, Philadelphia, Pa.) 0.006" thick, as described above, with a nominal inner diameter of 0.090" and a nominal outer diameter of 0.108". The tip and guide wire used in the catheter were as described above, and the balloon was of 0.003" nominal thickness. The balloon was furled to a diameter of 0.118" and could relax to about 0.124" diameter in its packaging sheath.

Testing

Kink tests and stiffness tests were conducted on inner and outer lumens and the combination of the two as described above, with only slightly different dimensions. The nitinol inner lumens tested had an inner diameter of 0.0283"±0.0003" and an outer diameter of 0.0347"±0.0003. The coextruded outer lumens had a nominal inside diameter of 0.090" and a nominal outside diameter of 0.106". Crush tests also were conducted on various outer lumens.

The kink tests utilized a template having multiple circles imprinted thereon, all with a common tangent point. The circles were 2", 1¾", 1½", 1¼", 1", ¾" and ½" in diameter. An appropriate length of each tubing being tested was formed into a larger loop and held against the template with the ends crossing and tangent to the circles at the aforenoted common tangent point. While maintaining this relationship to the template, one end of the looped tube was pulled to gradually reduce the loop diameter until the sample kinked. The diameter, also in inches, at which kinking occurred was recorded. When the tubing kinked between two circles, the average of those two circles was used as the kink diameter for calculations. In the case of outer lumen tubes, notes also were made of whether the kinking occurred quickly, moderately or slowly.

After examining a variety of potential 8 Fr outer lumens, seven coextrusions of polyurethane over nylon were tested, along with one 9 Fr outer lumen as described above for comparison purposes, using five samples of each. The following table reflects the average diameter, in inches, at which kinking occurred in each of these seven prospective outer lumens, the nature of the kinking action, and the average diameter, also in inches, at which the combination of the respective outer lumen tube and a nitinol inner lumen as described above kinked:

| Lumen-Coextrusion Materials | OUTER LUMEN ONLY | | COMBINED |
|---|---|---|---|
| | Diameter | Notes | Diameter |
| a. .003" nylon, .005" polyurethane | 1.38 | Moderate | 1.5 |
| b. .005" nylon, .003" polyurethane | 1.53 | Quickly | 1.6 |
| c. .004" nylon, .004" polyurethane | 1.65 | Quickly | 1.75 |
| d. .001" nylon, .007" polyurethane | 1.0 | Slowly | 1.15 |
| e. .002" nylon, .006" polyurethane | 1.05 | Slowly | 1.3 |
| f. .004" nylon .004" polyurethane (with barium sulfate) | 1.73 | Quickly | |
| g. .006" nylon, .002" polyurethane | 1.18 | Quickly | 1.33 |

The 9 Fr outer lumen tubes were of the aforedescribed current commercial design, being polyurethane tubes with an inner diameter of about 0.101" and an outer diameter of about 0.122". The average first kinking diameter for the 9 Fr outer lumen tubes was 1" and they kinked "slowly".

The three outer lumens with the best kink test results, namely coextrusions d, e and g, also were tested for crush resistance in hemovalves. The coextrusion g provided the best resistance to crushing by the valves.

Further samples of the construction g, namely coextrusion tubes of 0.002" polyurethane around 0.006" nylon, were subjected to further comparative tests with samples of the aforedescribed 9 Fr catheter lumen tubes, singly and in combination of the respective inner and outer lumen tubes. The average kink diameters in inches were as follows:

| | New 8 Fr | Current 9 Fr |
|---|---|---|
| Inner Lumen Tube* | Less than 0.5 | Less than 0.5 |
| Outer Lumen Tube | 1.35 | 1.15 |
| Combination of the Above | 1.19 | 1.15 |

*The nitinol tubes tested included both extruded tubes and drawn and machined tubes, with the results being substantially the same.

Thirty samples each of the new inner and outer lumen tubes and ten each of the inner and outer tubes of the current design were subjected to stiffness tests, both individually and with the respective inner and outer tubes assembled together, using a Tinius Olsen stiffness tester. The bending moments were calculated and used for comparisons. Since the areas of the 8 Fr and 9 Fr parts were different, the values were normalized by multiplying the 9 Fr results by the ratios of their areas. Selected comparison angles were chosen within the following parameters: (1) All samples achieved the angle; and (2) the test data had not started to decline, i.e., no indication of a kink forming in the sample. The average values in inch-pounds were as follows:

| | Bending Moment | Bending Moment |
|---|---|---|
| Inner Lumen | at 57 Degrees | |
| New Inner Lumen | 0.265 | |
| Current Inner Lumen | 0.014 | |
| Outer Lumen | at 27 Degrees | |
| New Outer Lumen | 0.168 | |
| Current Outer Lumen | 0.075 | |
| Combined Lumen | at 69 Degrees | at 57 Degrees |
| New Outer/Inner Lumen | 0.433 | 0.413 |
| Current Outer/Inner Lumen | 0.115 | 0.144 |

It will be seen that the constructions in a accordance with this invention attained the desired size reduction, while providing good kink resistance and attendant flexibility and increased stiffness.

Thin-walled balloons as alluded to above also were tested for operational strength, using thirty sample uncoated balloons with an average measured thickness of 0.0033" (range of 0.003" to 0.004") and thirty such balloons with a hydrophilic coating and therefor having an average measured thickness of 0.0037" (range of 0.003" to 0.004"). Tests using samples of the respective materials showed average yield strengths of 1070 psi for the uncoated material and 889 psi for the coated material. The corresponding internal pressures to generate yield pressures, in a 40 cc IAB for example, would be 11.15 psi for the uncoated material and 10.33 psi for the coated material.

Aneurysm tests also were conducted using such sample balloons which were adhered to outer lumens and leak tested prior to being subjected to aneurysm pressures. Pressure was increased in each balloon until a dramatic reduction of pressure was noted, indicating rapid expansion of the balloon membrane. The average aneuryzation pressures so measured were 13.6 psi for the uncoated balloons and 10.58 psi for the coated balloons. Thus, all were far above the normal usage pressure of about 150 mmHG or 2.9 psi for such balloons, by a factor of more than three.

It will be appreciated that improved intra-aortic balloon pump devices have been provided which meet the objects of this invention.

The invention has been described in considerable detail with reference to certain embodiments, and particularly with respect to the preferred embodiments thereof. However, it will be understood that variations, modifications and improvements may be made, particularly by those skilled in this art and in light of the teachings referred to herein, within the spirit and scope of the invention as claimed.

What is claimed is:

1. A method of forming intra-aortic balloons for assembly in vascular catheter systems comprising the steps of forming a balloon blank having a sleeve section at one end, stretching such sleeve section longitudinally to reduce the diameter thereof, heating said stretched sleeve section to relieve the stress in said sleeve section while so stretched, and cooling said sleeve section, thereby to preserve said sleeve section in its reduced diameter state wherein said balloon blank including said reduced diameter sleeve section forms said intra-aortic balloon.

2. The invention as in claim 1 wherein said balloon blank is formed of plastic by dip casting on a mandrel.

3. The invention as in claim 1 including the steps of forming said balloon blank by dip casting a plastic material on a mandrel with said sleeve section being formed on said mandrel at one end of said blank, and removing said blank from said mandrel by axial sliding over said mandrel in a direction wherein said sleeve section is stretched over said mandrel in the course of such removal.

4. The invention as in claim 1 wherein said stretching step is carried out by gripping a first portion of said balloon blank at the distal end of said sleeve section, gripping a second portion of said balloon blank at the opposite end of said sleeve section, and moving at least one of said gripped portions away from the other.

5. The invention as in claim 4 wherein said first portion is gripped between an internal mandrel and a surrounding clamp, and said second portion of said balloon is gripped in a clamp.

6. The invention as in claim 5 wherein stretching step is carried out prior to engagement of said second portion in said clamp.

7. The invention as in claim 5 wherein said stretching step is carried out by moving one of said mandrel and said clamp away from the other after said balloon portions are gripped therein.

8. The invention as in claim 4 and including positioning a heating element within said sleeve section, and wherein said heating step is effected by said heating element from within said sleeve section.

9. The invention as in claim 1 and wherein said heating step is effected by a heating element disposed interiorly of said sleeve section.

* * * * *